United States Patent [19]

Kuhla

[11] 4,006,142

[45] Feb. 1, 1977

[54] PREPARATION OF METHYL-3-(2-QUINOXALINYLME-THYLENE)CARBAZATE-$N^1$,$N^4$-DIOXIDE

[75] Inventor: Donald E. Kuhla, Gales Ferry, Conn.

[73] Assignee: Pfizer Inc., New York, N.Y.

[22] Filed: July 18, 1975

[21] Appl. No.: 597,209

Related U.S. Application Data

[62] Division of Ser. No. 338,906, March 7, 1973, Pat. No. 3,926,991.

[52] U.S. Cl. ............... 260/250 QN; 260/250 Q
[51] Int. Cl.$^2$ ................................. C07D 241/52
[58] Field of Search ............... 260/250 QN

[56] References Cited

UNITED STATES PATENTS

| | | | |
|---|---|---|---|
| 3,371,090 | 2/1968 | Johnston | 260/250 QN |
| 3,474,097 | 10/1969 | Johnston | 260/250 QN |
| 3,479,354 | 11/1969 | Galt | 260/250 QN |
| 3,485,836 | 12/1969 | Johnston | 260/250 QN |
| 3,759,912 | 9/1973 | Derungs | 260/250 QN |
| 3,926,991 | 12/1975 | Kuhla | 260/250 QN |

OTHER PUBLICATIONS

Emmons J.A.C.S. vol. 79, pp. 5739–5754 (1957).
Iinuma et al. Agr. Biol. Chem. 38, 2099–2105 (1974).

*Primary Examiner*—Donald G. Daus
*Assistant Examiner*—Mark L. Berch
*Attorney, Agent, or Firm*—Connolly and Hutz

[57] ABSTRACT

The novel process for the preparation of methyl 3-(2-quinoxalinylmethylene)carbazate $N^1$, $N^4$-dioxide which comprises contacting methyl 3-(2-quinoxalinylmethylene)carbazate with oxidizing agent in reaction-inert solvent at a temperature of from about 20° up to 100° C. until reaction is substantially complete, said oxidizing agent being selected from the group consisting of peracetic acid, perbenzoic acid, m-chloroperbenzoic acid, perphthalic acid, performic acid, trifluoroperacetic acid and hydrogen peroxide.

2 Claims, No Drawings

PREPARATION OF METHYL-3-(2-QUINOXALINYLMETHYLENE)-CARBAZATE-$N^1$,$N^4$-DIOXIDE

This application is a division of application Ser. No. 338,906 filed Mar. 7, 1973 and now U.S. Pat. 3,926,991.

BACKGROUND OF THE INVENTION

This invention relates to a novel synthetic procedure and more particularly to a novel method for the preparation of methyl 3-(2-quinoxalinylmethylene)carbazate $N^1$,$N^4$-dioxide. The compound prepared by the novel subject process is well known as a urinary tract antiseptic, systemic anti-infective, animal growth promotant as an agent for the control of chronic respiratory diseases in poultry and improvement of feed efficiency in animals. (Australian Vet. J. 48, No. 10 579, (1972) and Rec. Med. Vet. ecole Alfort 148 No. 3 365–73 (1972)).

SUMMARY OF THE INVENTION

Accordingly the present invention discloses a process for the preparation of methyl 3-(2-quinoxalinylmethylene)carbazate $N^1$,$N^4$-dioxide which comprises contacting methyl 3-(2-quinoxalinylmethylene)carbazate with at least about 2 equivalents of oxidizing agent in a reaction inert solvent at a temperature of from about 20° up to 100° C. until the reaction is substantially complete, said oxidzing agent being selected from the group consisting of peracetic acid, perbenzoic acid, m-chloroperbenzoic acid, perphthalic acid, performic acid, trifluoroperacetic acid and hydrogen peroxide, and recovery of the product. In the case of hydrogen peroxide a catalyst in usually employed. Suitable catalysts are tungstic acid, sodium tungstate, sodium vanadate, sodium molybdate, potassium tungstate, potassium molybdate, vanadium pentaoxide, zirconium dioxide, tungsten trioxide or molybdenum trioxide.

A particularly preferred embodiment of the herein described invention concerns the above process wherein said oxidizing agent is peracetic acid and said solvent is acetic acid, since both the reagent and solvent are inexpensive.

A second preferred embodiment of the herein described invention concerns the above process wherein said oxidizing agent is m-chloroperbenzoic acid and said solvent is chloroform.

In both of the above embodiments the reaction temperature is preferably maintained at less than 50° C.

The new reaction of the present invention is carried out in a reaction-inert solvent. An inert solvent for purposes of this invention contemplates any solvent which allows solubilization of the reactants and is free of adverse effect on the reagents and products under the conditions employed. Two preferred types include organic acids, such as acetic acid, and halogenated solvents, such as chloroform and methylene chloride. In some cases water may be employed. However, any solvent possessing the qualities set forth above will be satisfactory. The temperature at which the reaction is performed may vary from 30° to about 100° C. and for the most part the optimum temperature will vary with the choice of oxidizing agent. Depending upon the particular oxidizing agent and temperature, the reaction time can vary from a few minutes to as long as 24 hours. Generally, to ensure complete reaction the relatively long time periods are preferred. Optimum reaction conditions are readily determined by experiment.

The proportion of oxidizing agent relative to the starting carbazate may vary widely but for efficient conversion at least about two equivalents of oxidizing agent per mole of carbazate are preferred.

The product is a crystalline substance which precipitates from the reaction mixture. It is collected by suitable means and dried.

The valuable product of this invention exhibits activity as urinary tract systemic anti-infective in animals, including man, against a wide variety of microorganisms including Gram-positive and Gram-negative bacteria. It is especially valuable against Gram negative infection both in vitro and in vivo.

Further, the addition of a low level of the herein described Schiff base to the diet of animals, both ruminant and non-ruminant, such that these animals receive the product over an extended period of time, at a level of from about 0.04 mg./kg. to about 10 mg./kg. of body weight per day, especially over a major portion of their active growth period, results in an acceleration of the rate of growth and improved feed efficiency. Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals and other factors known to be required for the maximum healthy growth of such animals. The animals thus attain market size sooner and on less feed.

These feed compositions have been found to be particularly valuable and outstanding in the case of such animals as poultry, rats, hogs, swine, lambs, cattle, and the like. In some instances the degree of response may vary with respect to the sex of the animals. The products, may, of course, be administered in one component of the feed or they may be blended uniformly throughout a mixed feed; alternatively as noted above, they may be administered in an equivalent amount via the animal's water ration. It should be noted that a variety of feed components may be of use in the nutritionally balanced feeds.

PREPARATION I

A solution of 14.0 g (0.0886 mole) of 2-quinoxalinecarboxaldehyde (prepared by the method of Landquist and Silk, J. Chem. Soc. 1956, 2052), 100 ml of ethanol and 14.0 g (0.156 mole) of methylcarbazate is heated to reflux on a steam bath and is then allowed to stand at room temperature overnight. The product, methyl 3-(2-quinoxalinylmethylene)carbazate, crystallizes: yield 14.0 g (69%); m.p. 242°–244°.

EXAMPLE 1

To a solution of methyl 3-(2-quinoxalinylmethylene)carbazate (46 g, 0.20 mole) in glacial acetic acid (200 ml) is added, in a dropwise manner, 40% peracetic acid (76 g, 0.40 mole) with the rate of addition such to maintain the temperature below about 50° C.

The reaction mixture is allowed to stand for 12 hours and then diluted with water. The solid which precipitates is collected, washed with water and dried to give crystalline methyl 3-(2-quinoxalinylmethylene)carbazate $N^1$,$N^4$-dioxide.

EXAMPLE II

To a solution of methyl 3-(2-quinoxalinylmethylene)carbazate (46 g, 0.20 mole) in chloroform (300 ml) is added a solution of 85% m-chloroperbenzoic acid (82 g, 0.40 mole) in chloroform (300 ml). The reaction temperature is maintained below 50° C. by adjusting the rate of addition and using external cooling.

After stirring 24 hours, the mixture is filtered and the solid slurried with excess aqueous sodium bicarbonate to remove m-chlorobenzoic acid. The slurry is filtered and the solid washed with water and dried to give methyl 3-(2-quinoxalinylmethylene) carbazate $N^1,N^4$-dioxide as a crystalline solid.

EXAMPLE III

A mixture of methyl 3-(2-quinoxalinylmethylene)carbazate (23.0 g, 0.1 mole), tungstic acid (2.5 g) and 30 ml of t-butanol is heated to 60°-65°. An aqueous solution of 30% hydrogen peroxide (30 ml) is added over several minutes. After 2.5 hours, the mixture is cooled and is then diluted with 200 ml of water. The crystalline methyl 3-(2-quinoxalinylmethylene)carbazate $N^1,N^4$-dioxide is filtered, washed with water and dried.

What is claimed is:

1. A process for the preparation of methyl-3-(2-quinoxalinylmethylene)carbazate $N^1,N^4$-dioxide which comprises the step of reacting methyl-3-(2-quinoxalinylmethylene) carbazate with two equivalents of m-chloroperbenzoic acid in a reaction inert solvent at a temperature of from about 20° up to 100° C. until reaction is substantially complete.

2. The process of claim 1 wherein said reaction inert solvent is chloroform.

* * * * *